United States Patent
Ogasawara

(10) Patent No.: US 10,384,073 B2
(45) Date of Patent: Aug. 20, 2019

(54) SKIN WOUND HEALING AND HAIR GROWTH

(71) Applicant: Mignon Belle Co., Ltd., Osaka-shi, Osaka (JP)

(72) Inventor: Masahiro Ogasawara, Osaka (JP)

(73) Assignee: Mignon Belle Co., Ltd., Osaka (JP)

( * ) Notice: Subject to any disclaimer, the term of this patent is extended or adjusted under 35 U.S.C. 154(b) by 240 days.

(21) Appl. No.: 14/690,395

(22) Filed: Apr. 18, 2015

(65) Prior Publication Data

US 2015/0217134 A1    Aug. 6, 2015

Related U.S. Application Data

(63) Continuation of application No. 13/499,690, filed as application No. PCT/JP2010/007067 on Dec. 3, 2010, now abandoned.

(30) Foreign Application Priority Data

Dec. 3, 2009   (JP) .................................. 2009-275964
Aug. 7, 2010   (JP) .................................. 2010-178217

(51) Int. Cl.
   *A61N 5/06*    (2006.01)
(52) U.S. Cl.
   CPC ......... *A61N 5/0622* (2013.01); *A61N 5/0617* (2013.01); *A61N 5/0616* (2013.01); *A61N 2005/0652* (2013.01); *A61N 2005/0662* (2013.01); *A61N 2005/0663* (2013.01)
(58) Field of Classification Search
   CPC ...... A61N 5/06; A61N 5/0613; A61N 5/0616; A61N 5/0617; A61N 5/062; A61N 2005/0627; A61N 2005/0642; A61N 2005/0643; A61N 2005/0644; A61N 2005/0658; A61N 2005/0662;
   (Continued)

(56) References Cited

U.S. PATENT DOCUMENTS 8,968,221 B2    3/2015   Pryor et al.
2003/0004556 A1*   1/2003   McDaniel ............. A61K 8/494
                                                           607/88
(Continued)

*Primary Examiner* — Ahmed M Farah
(74) *Attorney, Agent, or Firm* — Ogilvie Law Firm

(57) ABSTRACT

Disclosed are devices and methods that can help heal skin wounds and grow hair by irradiating light from light emitting diodes (LED). One device is provided with: an ultra-narrowband light irradiation means which generates ultra-narrowband red light with peak wavelength range 620-660 nm and FWHM 10 nm or less; an ultra-narrowband light irradiation means which generates ultra-narrowband green light with peak wavelength range 500-540 nm and FWHM 10 nm or less; an ultra-narrowband light irradiation means which generates ultra-narrowband blue light with peak wavelength range 440-480 nm and FWHM 10 nm or less; and an ultra-narrowband light irradiation means which generates ultra-narrowband red to near infrared light with peak wavelength range 700-2500 nm and FWHM 10 nm or less. In this way, cell growth factors such as HGF and KGF are acted upon by irradiating the affected area with ultra-narrowband monochromatic light of FWHM 10 nm or less, which has excellent effects in healing skin wounds and growing hair.

6 Claims, 21 Drawing Sheets

(58) Field of Classification Search
CPC .......... A61N 2005/0663; A61B 18/203; A61B 2018/00452; A61B 2018/00476
USPC ................ 607/88–91; 606/3, 9, 10; 128/898
See application file for complete search history.

(56) References Cited

U.S. PATENT DOCUMENTS

| | | | |
|---|---|---|---|
| 2004/0162596 A1* | 8/2004 | Altshuler | A61N 5/0616 607/88 |
| 2005/0283211 A1 | 12/2005 | McDaniel | |
| 2006/0030908 A1 | 2/2006 | Powell et al. | |
| 2006/0212025 A1* | 9/2006 | McDaniel | A61B 18/203 606/9 |
| 2006/0217690 A1* | 9/2006 | Bastin | A61N 5/0616 606/9 |
| 2008/0039826 A1* | 2/2008 | Scheibner | A61B 18/203 606/9 |
| 2008/0269732 A1* | 10/2008 | Pyun | A61N 5/0616 606/9 |
| 2009/0054953 A1 | 2/2009 | Whitehurst | |
| 2010/0152645 A1* | 6/2010 | Ogasawara | A61N 1/30 604/20 |
| 2012/0123305 A1* | 5/2012 | Pearl | A61N 5/0617 601/15 |

* cited by examiner

SKIN WOUND HEALING AND HAIR GROWTH

RELATED APPLICATIONS

The present application is a continuation of U.S. patent application Ser. No. 13/499,690 filed Mar. 31, 2013, which in turn is a national entry under 35 USC 371 of PCT/JP2010/007067 (WO 2011/067941), with priority further claimed to JP 2009-275964 filed 3 Dec. 2009 and JP 2010-178217 filed 7 Aug. 2010. U.S. patent application Ser. No. 13/499,690 filed Mar. 31, 2013 is incorporated herein by reference in its entirety.

TECHNICAL FIELD

The present invention relates to a device that has excellent effects on skin wound healing and hair restoration.

BACKGROUND ART

A conventionally known medical laser treatment device for relieving chronic pain in muscles, joints, etc., is, for example, a device that uses a semiconductor laser emitting near-infrared rays with a wavelength of 780 to 830 nm and having a laser beam output of 10 to 60 mW (Patent Document 1). The device comprises photosensors for detecting reflected light of a laser beam applied to the skin surface of the affected area. The photosensors are configured to detect the reflected light of the laser beam only when the laser beam irradiation port of the probe is in contact with the skin surface. When at least one of the photosensors does not detect laser reflected light, the laser beam irradiation is stopped.

Another known device is a near-infrared LED treatment device that can relieve various diseases, such as periarthritis humeroscapularis (frozen shoulder), muscular pain, gout, stiff shoulder, lumbago, rheumatoid arthritis, gonarthrosis, bruise, sprain, postherpetic neuralgia, pain in wound area, stress, and various other pains and swellings, by applying and permeating near-infrared rays from a light source that is a near-infrared light-emitting diode with a wavelength having excellent permeability into body tissue. The device can promote blood circulation and increase resistance, and has high safety (Patent Document 2).

[Patent Document 1] JP 1993-057026 A
[Patent Document 2] JP 2009-207605 A

DISCLOSURE OF THE INVENTION

Problems to be Solved by the Invention

As described above, conventional devices are mainly laser treatment devices. Although there are near-infrared LED treatment devices using light-emitting diodes (LEDs), light itself does not have excellent effects on skin wound healing, and blood circulation promotion and resistance increase are accomplished by the action of near-infrared rays. Under such circumstances, there are no known devices that can heal skin wounds by light irradiation using ultra-narrowband monochromatic light.

An object of the present invention is to provide a device that can heal skin wounds by irradiation of LED light.

Means to Solve the Objects

The inventor of the present invention is a medical doctor who specializes in cosmetic dermatological treatment, providing information regarding hair restoration, hair growth and prevention of hair loss, and consulting services regarding the above. Through such services, the present inventor has continued extensive research on skin improvement methods and hair restoration and hair growth methods that are so safe that no trouble occurs in the skin after a long period of use, and that can achieve a sufficient effect in a short time.

As a result of various trials, the present inventor found that when the affected area was actually irradiated with an ultra-narrowband monochromatic light having a half-band width of 10 nm or less in his own beauty clinic, stronger effects were obtained than when a light of a similar wavelength and the same intensity was used. The present inventor also found that the affected area was irradiated with an ultra-narrowband monochromatic light having a half-band width of 10 nm or less to remarkably reduce light interference of the light from the light source, and that the effects and actions inherent in the monochromatic light can be exerted on skin cells and subcutaneous cells.

Furthermore, the present inventor found that the affected area is irradiated with an ultra-narrowband monochromatic light having a half-band width of 10 nm or less to thereby activate growth factors, such as HGF and KGF, and exhibit excellent healing effects on skin wounds. The present invention has been accomplished based on these findings.

More specifically, the skin wound healing device of the present invention comprises an ultra-narrowband light irradiation means for generating an ultra-narrowband red light having a peak wavelength of 620 nm to 660 nm and a half-band width of 10 nm or less (red light to near-infrared light).

Moreover, the skin wound healing device of the present invention comprises an ultra-narrowband light irradiation means for generating an ultra-narrowband green light having a peak wavelength of 500 nm to 540 nm and a half-band width of 10 nm or less.

Moreover, the skin wound healing device of the present invention comprises an ultra-narrowband light irradiation means for generating an ultra-narrowband blue light having a peak wavelength of 440 nm to 480 nm and a half-band width of 10 nm or less.

Moreover, the skin wound healing device of the present invention comprises an ultra-narrowband light irradiation means for generating an ultra-narrowband red light to near-infrared light having a peak wavelength of 700 nm to 2500 nm and a half-band width of 10 nm or less.

Here, it is preferable that the above skin wound healing device further comprises, in addition to the ultra-narrowband light irradiation means, a diffusing means for diffusing the light emitted from the ultra-narrowband light irradiation means.

Next, the hair restoration device of the present invention comprises an ultra-narrowband red light irradiation means for generating an ultra-narrowband red light having a peak wavelength of 600 to 900 nm (orange light to light close to infrared), preferably 630 to 650 nm, and having a half-band width of 10 nm or less; the hair restoration device applying the ultra-narrowband red light to a head for a predetermined time at a predetermined power level so that the irradiation energy is not greater than a predetermined value, thereby changing the mRNA expression levels of cytokines secreted from hair papilla cells and promoting hair restoration.

Specific cytokines, the mRNA expression levels of which are to be changed, are HGF (Hepatocyte Growth Factor), IGF (Insulin-like growth factors), leptin, and VEGF (Vascular Endothelial Growth Factor), which are cell growth factors. The mRNA expression levels of all of these cytokines increase within 24 hour after irradiation.

In addition, while the mRNA expression levels of the above cytokines are increased, the mRNA expression level of TNF-α, which is an inflammatory cytokine, is decreased within eight hours.

Such an ultra-narrowband red light irradiation means preferably uses a light-emitting diode (LED) to reduce the irradiation energy so that side effects and complications are prevented.

Effects of the Invention

The above skin wound healing device, which can apply an ultra-narrowband red or green light, more strongly induces proliferation of leptin, compared to the irradiation of alight with a broad half-band width.

The above skin wound healing device, which can apply an ultra-narrowband red, green, or blue light, more strongly induces proliferation of HGF (Hepatocyte Growth Factor), which contributes to angiogenesis and skin wound healing, compared to the irradiation of a light with a broad half-band width.

The above skin wound healing device, which can apply an ultra-narrowband red, green, or blue light, more strongly induces proliferation of KGF (Keratinocyte Growth Factor), which is a keratinocyte growth factor, compared to the irradiation of a light with a broad half-band width.

The above red light-emitting skin wound healing device strongly induces proliferation of VEGF (Vascular Endothelial Growth Factor), which is a vascular endothelial growth factor, compared to the irradiation of a light with a broad half-band width. That is, the skin wound healing device of the present invention activates growth factors, such as HGF and KGF, and exhibits excellent healing effects on skin wounds, compared to conventional optical treatment devices.

Moreover, the skin wound healing device of the present invention comprises:

an ultra-narrowband light irradiation means for generating an ultra-narrowband red light having a peak wavelength of 620 to 660 nm and a half-band width of 10 nm or less;

an ultra-narrowband light irradiation means for generating an ultra-narrowband green light having a peak wavelength of 500 to 540 nm and a half-band width of 10 nm or less;

a diffusing means for diffusing the light emitted from the ultra-narrowband light irradiation means; and a switching means for alternately switching the red light irradiation and the green light irradiation. As a result of trial and error, the present inventor found that the red and green lights effectively acted on skin wound healing. When the red and green lights were simultaneously applied, their wavelengths interfered with each other, suppressing the effect of each wavelength. Accordingly, the red and green lights were applied not simultaneously but alternately, thereby achieving the maximum effect of each wavelength. Here, the switching means for alternately switching the red light irradiation and the green light irradiation is designed, for example, to switch the power switches of the ultra-narrowband red light irradiation means and the ultra-narrowband green light irradiation means that are arranged adjacent to each other.

The hair restoration device of the present invention increases the mRNA expression levels of all of the cell growth factors, i.e., HGF (Hepatocyte Growth Factor), IGF (Insulin-like growth factors), leptin, and VEGF (Vascular Endothelial Growth Factor), within 24 hours after light irradiation, while reducing the mRNA expression level of TNF-α, which is an inflammatory cytokine, within eight hours. Thus, the hair restoration device of the present invention has an effect of promoting hair restoration.

Moreover, the hair restoration device of the present invention has an effect of preventing side effects and complications when used in the human body. Furthermore, the hair restoration device of the present invention has a high penetration depth into the scalp, and thus has an effect of sufficiently affecting hair papilla cells under the scalp.

BEST MODE FOR CARRYING OUT THE INVENTION

Hereinafter, an embodiment of the present invention will be described with reference to the accompanying drawings. The present invention is not limited to the illustrated construction. The present invention can be variously changed in design.

Embodiment 1

Figure 1:
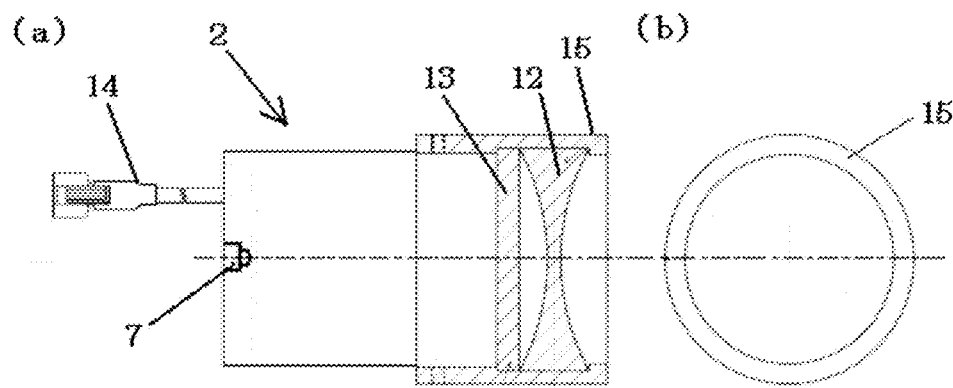
FIG. 1 is a diagram of the ultra-narrowband light irradiation device of the present invention.

FIG. 1 schematically illustrates the ultra-narrowband light irradiation device of the present invention. The ultra-narrowband light irradiation device of the present invention can deliver three different ultra-narrowband lights. The three different ultra-narrowband lights are a blue light (light having a peak wavelength of 456 nm and a half-band width of 10 nm), a green light (light having a peak wavelength of 518 nm and a half-band width of 8 nm), and a red light (light having a peak wavelength of 638 nm and a half-band width of 10 nm). Each of the ultra-narrowband lights is formed by a monochrome LED light source 7 (either of a red LED light source, a blue LED light source, or a green LED light source), a band-pass filter 13 for narrowing the wavelength band of each light emitted from the monochrome LED light source 7, and a diffusing lens 12 for diffusing the ultra-narrowband light having a half-band width of 10 nm passing through the band-pass filter 13.

Here, the monochromatic LED light source 7 may include a parallel light LED light source IBF-LS of IMAC CO., Ltd. The light irradiated from the monochromatic light source 7 is an ultra-long cast light with directionality. Diameter of the light is approximately 5 cm and this light is diffused via the diffusion lens 12.

These three different ultra-narrowband lights were applied to normal human dermal fibroblasts, and cell growth was observed.

The cells used were normal human dermal fibroblasts cultured at 37° C. in 10% FCS-DMEM in a 5% carbon dioxide environment. After the cell-cycle transition from metaphase to anaphase, the cell incubator was changed to DMEM. The resulting samples were subjected to mRNA analysis by RT-PCR assay. Table 1 below shows the analysis results. Table 1 shows growth factors and an inflammatory cytokine.

TABLE 1

| Growth Factor | Inflammatory Cytokine |
|---|---|
| HGF | IL-8 |
| KGF | |
| Leptin | |
| VEGF | |

As shown in Table 1 above, the irradiation part (light source) of each of the three different ultra-narrowband lights, i.e., the blue light (light having a peak wavelength of 456 nm and a half-band width of 10 nm), the green light (light having a peak wavelength of 518 nm and a half-band width of 8 nm), and the red light (light having a peak wavelength of 638 nm and a half-band width of 10 nm), was placed in a distance of 10 cm from fibroblasts, and the fibroblasts were irradiated with each light for 20 minutes without any control. Here, the illumination of the blue light (456 nm) was 140 luxs, the illumination of the green light (518 nm) was 520 luxs, and the illumination of the red light (638 nm) was 650 luxs. The illuminometer used in the measurement was a TOPCOM (registered trademark) illuminometer IM-5.

Zero hour (immediately), four hours, eight hours, and twenty-four hours after light irradiation, the cells were taken out from the cell incubator, and the mRNA expression levels of KGF, HGF, leptin, VEGF, and IL-8 were analyzed by RT-PCR assay.

Next, the results of protein concentration analysis by the ELISA (Enzyme-Linked Immunosorbent Assay) method are described. Similarly, the irradiation part (light source) of each of the blue light (456 nm), green light (518 nm), or red light (638 nm) was placed in a distance of 10 cm from fibroblasts, and the fibroblasts were irradiated with each light for 20 minutes without any control. One day, two days, three days, and four days after light irradiation, protein concentration was analyzed by the ELISA method.

The following shows the analysis results of protein concentration. Table 2 below shows the analysis of mRNA by RT-PCR. As is clear from Table 2, leptin, HGF, KGF, and VEGF are affected by the irradiation of the three different ultra-narrowband lights.

In particular, it was found that fibroblasts irradiated with the ultra-narrowband red or green light showed a higher leptin expression level than the control fibroblasts, regardless of the exposure dose. It is also found that the mRNA expression levels of HGF and KGF are strongly induced by the irradiation of any of the blue, green, and red lights. However, fibroblasts irradiated with the ultra-narrowband blue or green light showed less growth of IL-8 and VEGF than the control fibroblasts.

TABLE 2

| | Red light(638 nm) | | | | Green light(518 nm) | | | | Blue light(456 nm) | | | |
|---|---|---|---|---|---|---|---|---|---|---|---|---|
| | 1/3 | 4 | 8 | 24 hr | 1/3 | 4 | 8 | 24 hr | 1/3 | 4 | 8 | 24 hr |
| HGF | → | → | ↑ | ↑ | ↑ | ↑ | ↑ | ↑ | ↑ | ↑ | ↑ | ↑ |
| KGF | ↑ | ↑ | ↑ | ↑ | → | → | ↑ | ↑ | → | → | ↑ | ↑ |
| Leptin | ↑ | ↑ | ↑ | ↑ | → | ↑ | ↑ | ↑ | → | ↑ | ↑ | → |
| VEGF | → | → | ↑ | ↑ | → | ↓ | ↑ | ↑ | ↓ | ↓ | → | → |
| IL-8 | ↑ | ↑ | ↑ | → | → | → | ↓ | → | → | → | ↓ | → |

FIGS. 3 to 7 show the analysis results of protein concentration by ELISA. FIGS. 3 to 7 respectively show the analysis results of HGF, KGF, VEGF, and leptin. HGF, KGF, and VEGF increased by the irradiation of any of the blue, green, and red lights. However, leptin was less affected by the irradiation of the blue light, but was strongly induced by the irradiation of the red and green lights.

Thus, from the fact that HGF, KGF, VEGF, and leptin increased by the irradiation of the ultra-narrowband light, it was suggested that the irradiation of the ultra-narrowband light was effective for skin wound healing.

The blue light (456 nm), green light (518 nm), and red light (638 nm) can penetrate deeply into the skin, depending on their wavelengths, to affect not only keratin-producing cells but also fibroblasts.

Figure 2:
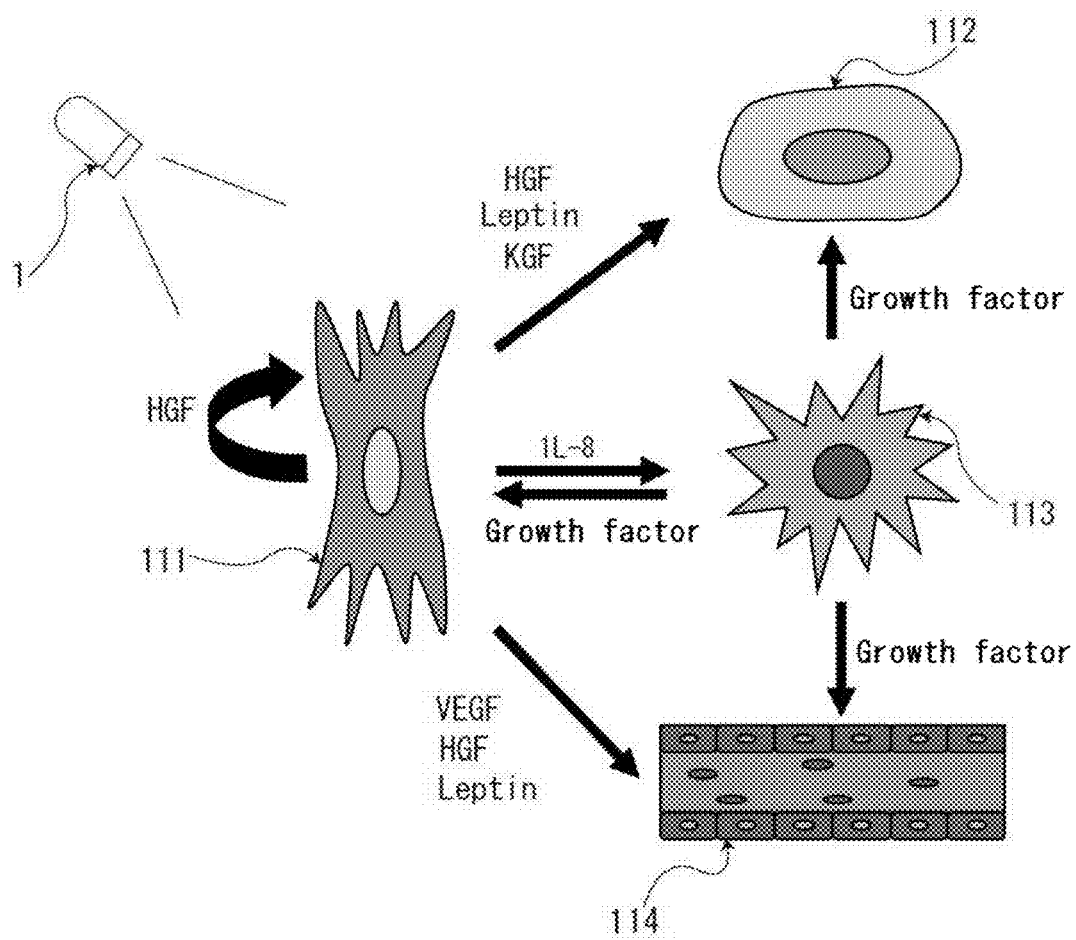
FIG. 2 is a drawing showing the influence of ultra-narrowband light on skin wound healing.

FIG. 2 shows the influence of ultra-narrowband light irradiation on skin wound healing. As shown in the figure, fibroblasts 111 promotes the increase of growth factors by an ultra-narrowband light irradiation means 1, and exerts influence on keratin-producing cells 112, macrophages 113, and endothelial cells 114. The present invention has an advantage of promoting healing of a skin wound by irradiating the wound with an ultra-narrowband light to strongly induce cytokines from fibroblasts.

Embodiment 2

Next, Example 2 explains that using an ultra-narrowband red light irradiation means for generating ultra-narrowband red light having a peak wavelength of 630 nm to 650 nm and a half-band width of 10 nm or less, the ultra-narrowband red light is applied to a head for a predetermined time at a predetermined power level so that the irradiation energy is not greater than a predetermined value, thereby changing the mRNA expression levels of cytokines secreted from hair papilla cells and promoting hair restoration.

First, the results of irradiating hair papilla cells with ultra-narrowband red, green, and blue lights having a half-band width of 10 nm or less using the ultra-narrowband light irradiation means are shown. Next, the results of actually irradiating human heads with ultra-narrowband red, green, and blue lights having a half-band width of 10 nm or less are shown.

Here, the irradiation lights of the ultra-narrowband light irradiation means are, as with Example 1, a blue light (light having a peak wavelength of 456 nm and a half-band width of 10 nm), a green light (light having a peak wavelength of 518 nm and a half-band width of 8 nm), and a red light (light having a peak wavelength of 638 nm and a half-band width of 10 nm). Moreover, as with Example 1, the ultra-narrowband light irradiation means comprises a monochrome light-emitting diode (LED) light source of each of the red, green, and blue lights, a band-pass filter for narrowing the wavelength band of each light emitted from the monochrome LED light source, and a diffusing lens for diffusing the ultra-narrowband light having a half-band width of 10 nm passing through the band-pass filter. The irradiation energy intensities of the red, green, and blue lights are 0.6, 0.2, and 0.3 (J/cm$^2$), respectively, when each light is applied for 20 minutes in a distance of 10 cm from the irradiation light source.

First, the results of irradiating hair papilla cells with the ultra-narrowband red, green, and blue lights having a half-band width of 10 nm or less using the ultra-narrowband light irradiation means are shown. In the experimental method, normal human hair papilla cells were cultured in a 35-mm dish using 10% FCS DMEM. Then, the cells were transferred to phenol red-free DMEM immediately before LED irradiation, and LED was applied for 20 minutes in a distance of 10 cm from the bottom of the dish. Each of the ultra-narrowband red, green, and blue lights having a half-band width of 10 nm or less was applied. RNA was extracted immediately, 4 hours, 8 hours, and 24 hours after irradiation, and the mRNA levels of cell growth factors, inflammatory cytokines, etc., were measured semi-quantitatively by the RT-PCR assay. Table 3 below summarizes the measurement results of cytokines, the changes of which were observed by the RT-PCR assay.

TABLE 3

| | Red light(638 nm) | | | | Green light(518 nm) | | | | Blue light(456 nm) | | | |
|---|---|---|---|---|---|---|---|---|---|---|---|---|
| | 0 | 4 | 8 | 24 hr | 0 | 4 | 8 | 24 hr | 0 | 4 | 8 | 24 hr |
| HGF | → | → | → | ↑ | → | ↑ | → | → | → | ↑ | ↑ | ↑ |
| IGF | → | ↑ | ↑ | ↑ | → | → | ↑ | → | → | → | → | → |
| Leptin | → | ↑ | ↑ | → | → | ↑ | ↑ | → | → | ↑ | → | ↑ |
| VEGF | ↑ | ↑ | ↑ | → | ↑ | → | ↑ | → | → | → | → | ↑ |
| TNF-α | → | ↓ | ↓ | → | → | → | ↓ | → | → | → | → | → |

From Table 3 above, regarding the cell growth factor cytokine HGF (Hepatocyte Growth Factor), in the case of the irradiation of the ultra-narrowband red light having a half-band width of 10 nm or less, the mRNA expression level increased 24 hours later after irradiation, compared to the control group. In the case of the irradiation of the ultra-narrowband green light having a half-band width of 10 nm or less, the mRNA expression level increased 4 hours after irradiation. In the case of the irradiation of the ultra-narrowband blue light having a half-band width of 10 nm or less, the mRNA expression level increased 4 hours, 8 hours, and 24 hours after irradiation.

Regarding the cell growth factor cytokine IGF-1 (Insulin-like Growth Factor-1), in the case of the irradiation of the ultra-narrowband red light having a half-band width of 10 nm or less, the mRNA expression level increased 4 hours, 8 hours, and 24 hours after irradiation. In the case of the irradiation of the ultra-narrowband green light having a half-band width of 10 nm or less, the mRNA expression level increased immediately and 8 hours after irradiation. In the case of the irradiation of the ultra-narrowband blue light having a half-band width of 10 nm or less, the mRNA expression level was not changed significantly.

Regarding the cell growth factor cytokine leptin, in the case of the irradiation of the ultra-narrowband red light having a half-band width of 10 nm or less, the mRNA expression level increased 4 hours and 8 hours after irradiation. In the case of the irradiation of the ultra-narrowband green light having a half-band width of 10 nm or less, the mRNA expression level also increased 4 hours and 8 hours after irradiation, as with the red light irradiation. In the case of the irradiation of the ultra-narrowband blue light having a half-band width of 10 nm or less, the mRNA expression level increased immediately, 4 hours, and 24 hours after irradiation.

Regarding the cell growth factor cytokine VEGF (Vascular Endothelial Growth Factor), in the case of the irradiation of the ultra-narrowband red light having a half-band width of 10 nm or less, the mRNA expression level increased immediately, 4 hours, and 8 hours after irradiation. In the case of the irradiation of the ultra-narrowband green light having a half-band width of 10 nm or less, the mRNA expression level increased immediately and 8 hours after irradiation. In the case of the irradiation of the ultra-narrowband blue light having a half-band width of 10 nm or less, the mRNA expression level increased immediately and 24 hours after irradiation.

Regarding the inflammatory cytokine TNF-α (Tumor Necrosis Factor-α), in the case of the irradiation of the ultra-narrowband red light having a half-band width of 10 nm or less, the mRNA expression level decreased 4 hours and 8 hours after irradiation. In the case of the irradiation of the ultra-narrowband green light having a half-band width of 10 nm or less, the mRNA expression level decreased 8 hours after irradiation.

Figure 8:
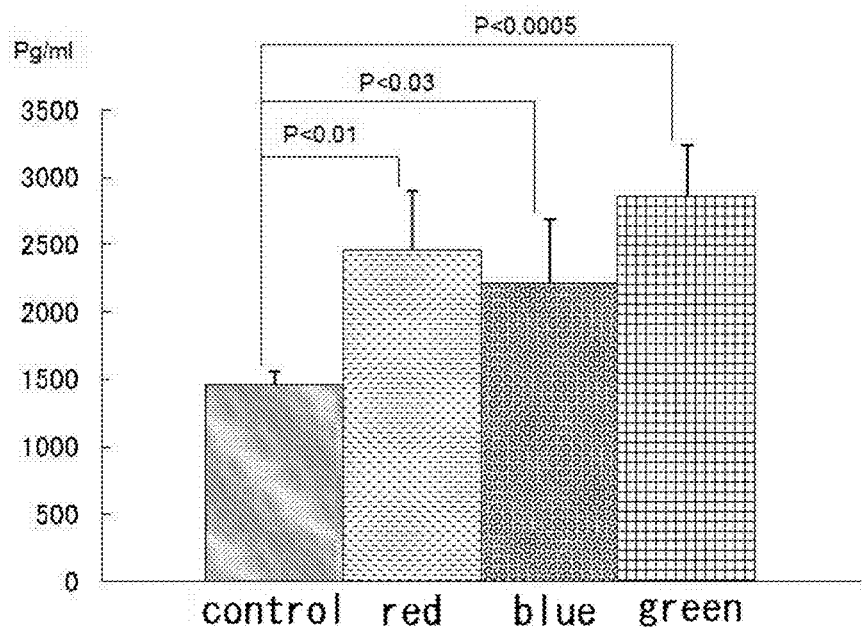
FIG. 8 is a graph showing the HGF protein concentration of a fibroblast culture supernatant (analysis results by the ELISA method).
Figure 9:
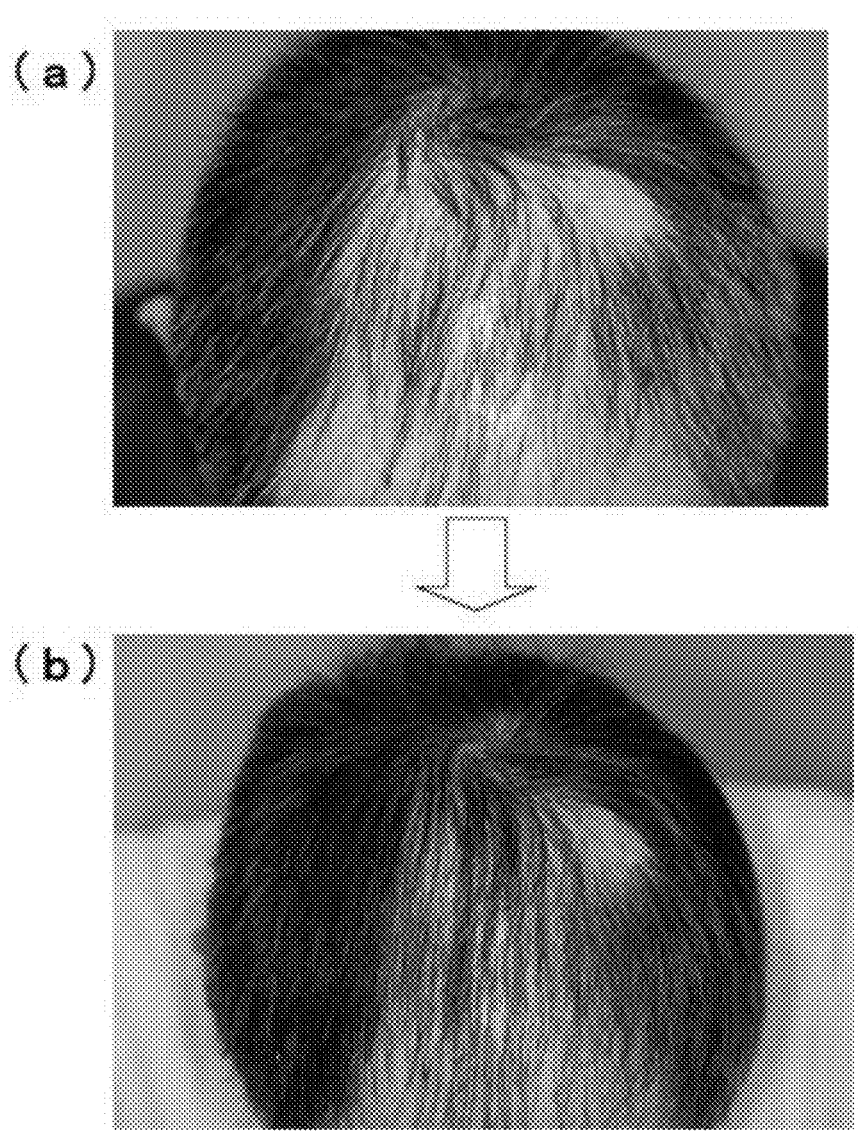
FIG. 9 is the status of the progress of hair restoration of male monitors 1.
Figure 10:
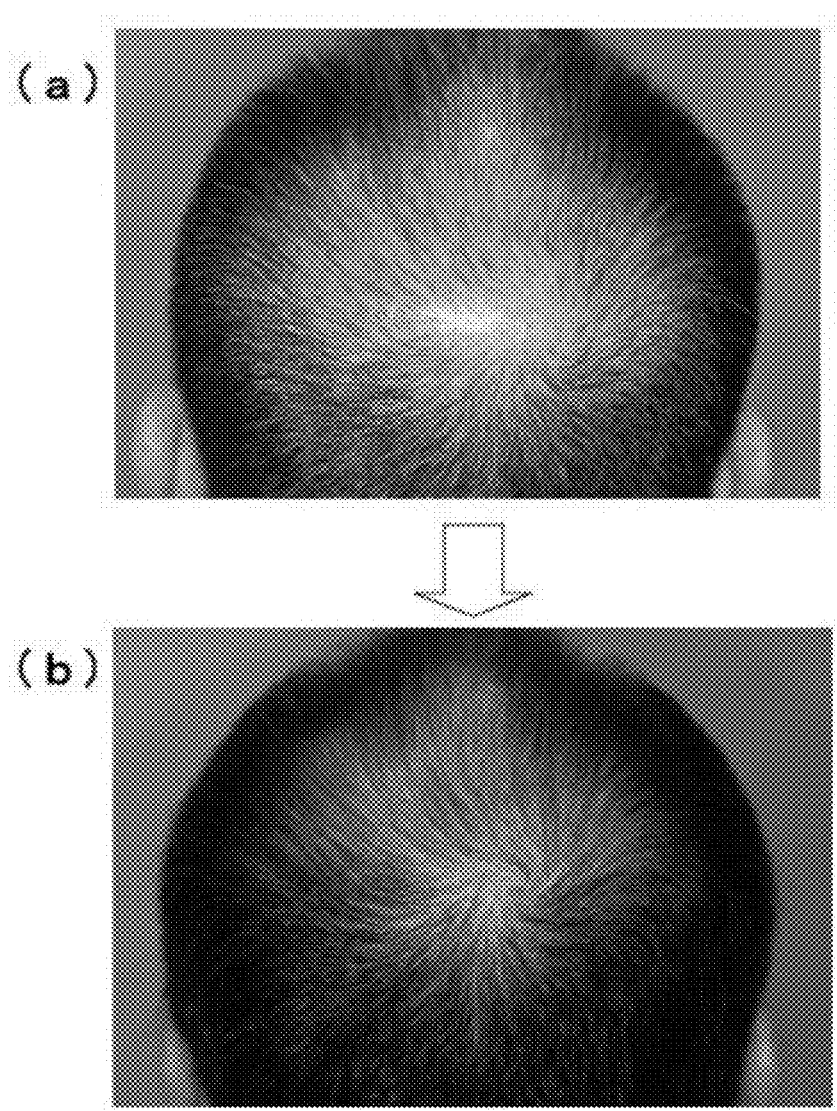
FIG. 10 is the status of the progress of hair restoration of male monitors 2.
Figure 11:
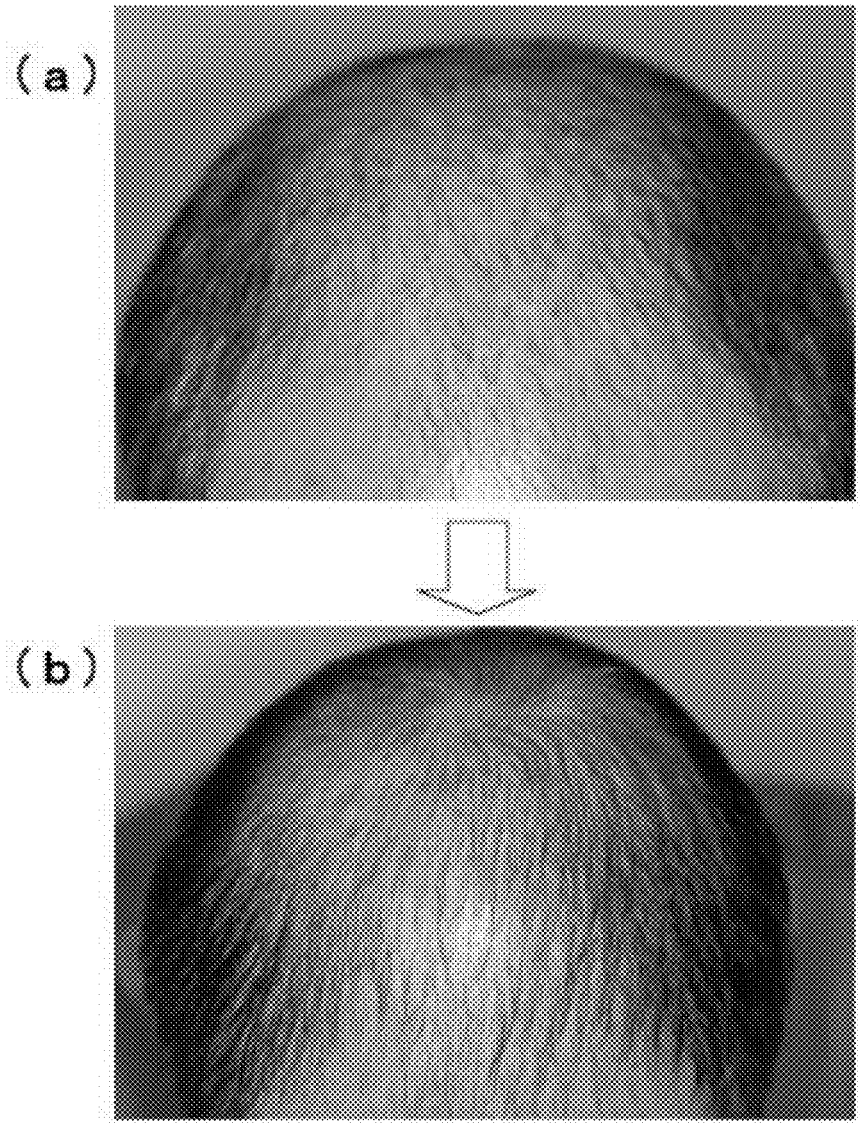
FIG. 11 is the status of the progress of hair restoration of male monitors 3.
Figure 12:
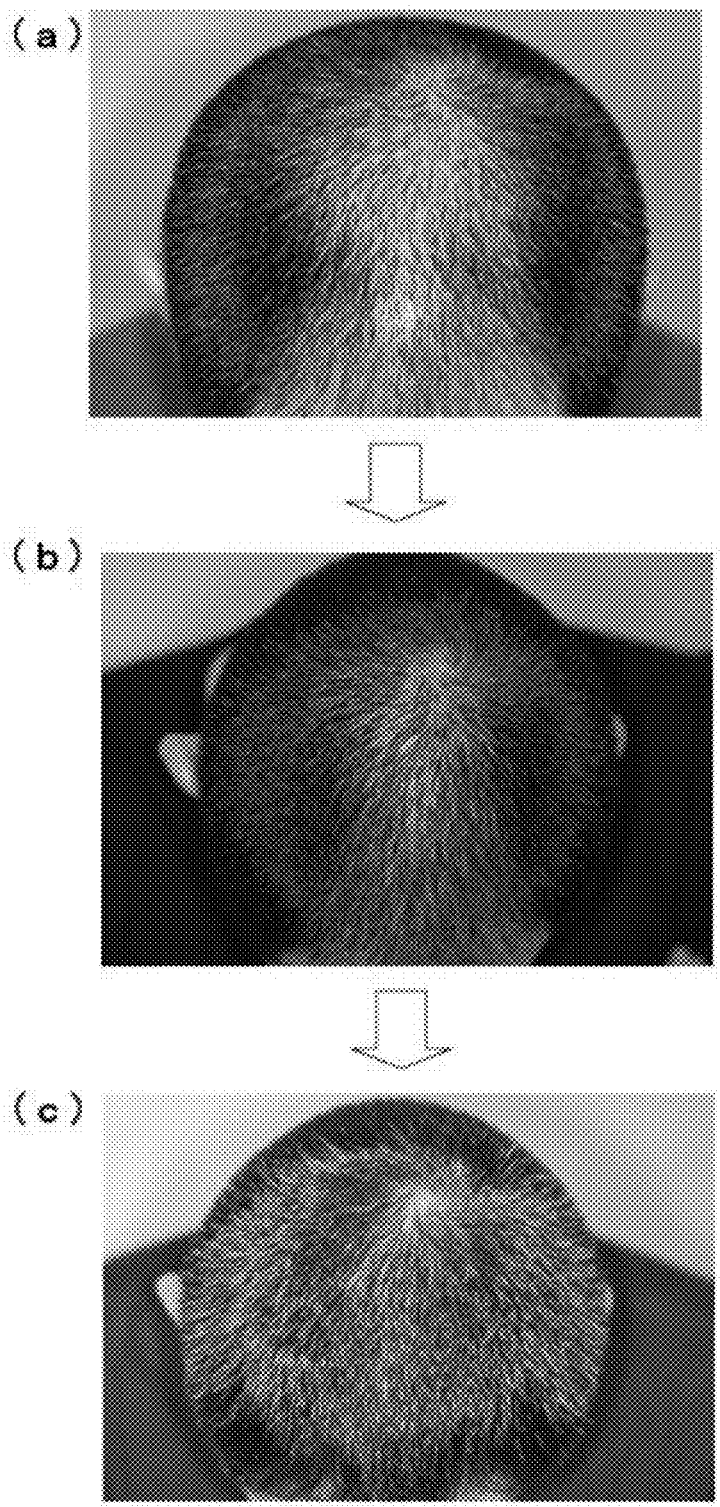
FIG. 12 is the status of the progress of hair restoration of male monitors 4.
Figure 13:
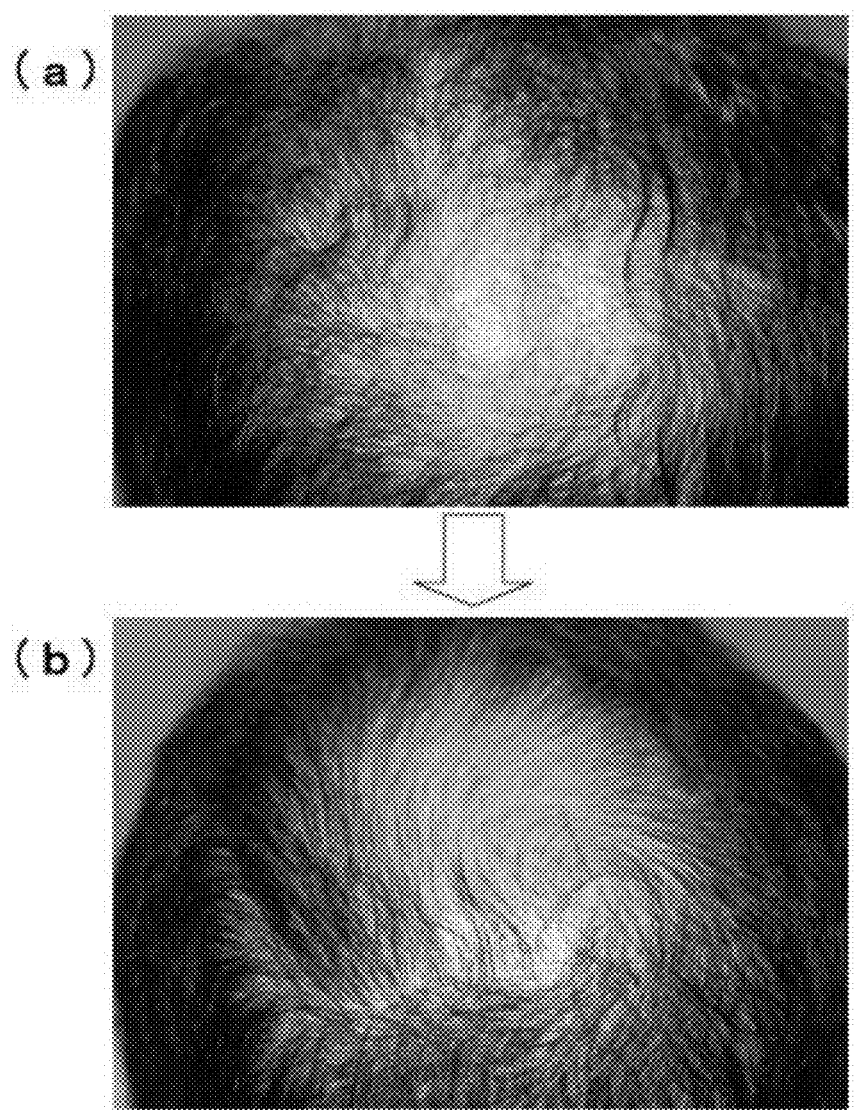
FIG. 13 is the status of the progress of hair restoration of male monitors 5.
Figure 14:
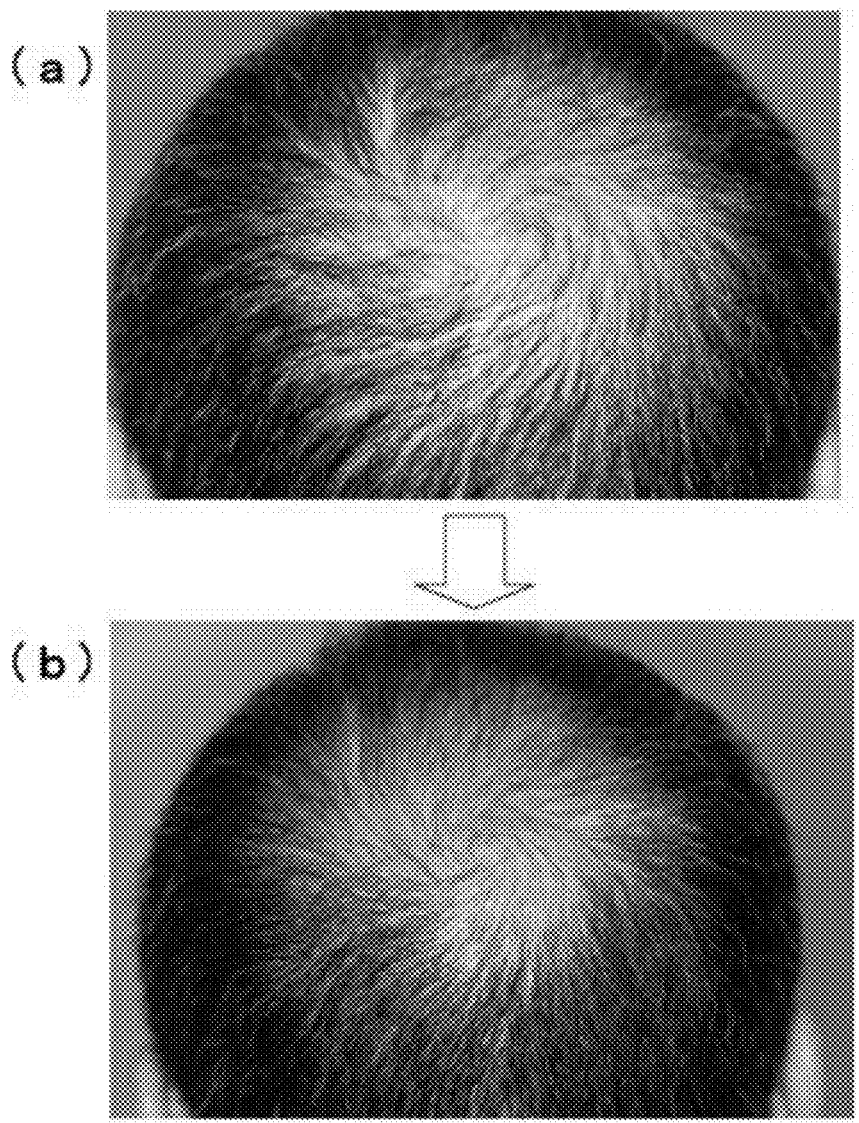
FIG. 14 is the status of the progress of hair restoration of male monitors 6.
Figure 15:
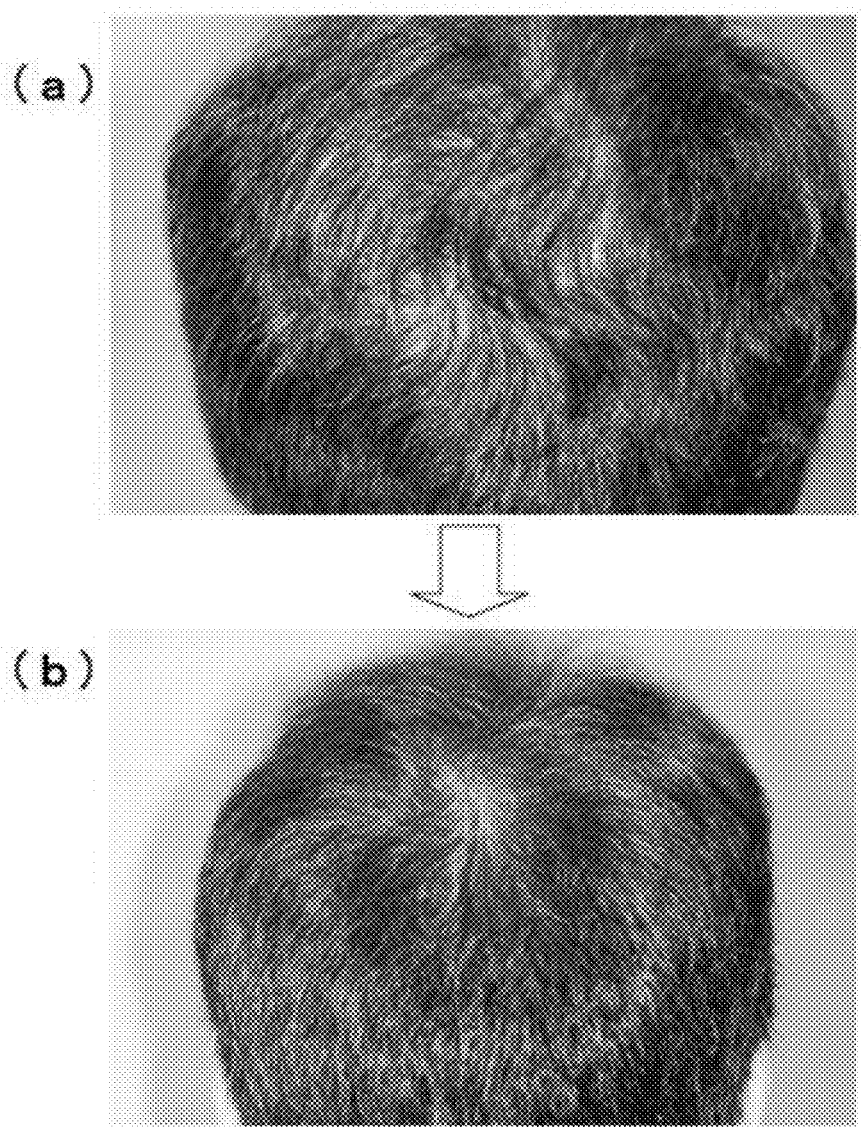
FIG. 15 is the status of the progress of hair restoration of male monitors 7.
Figure 16:
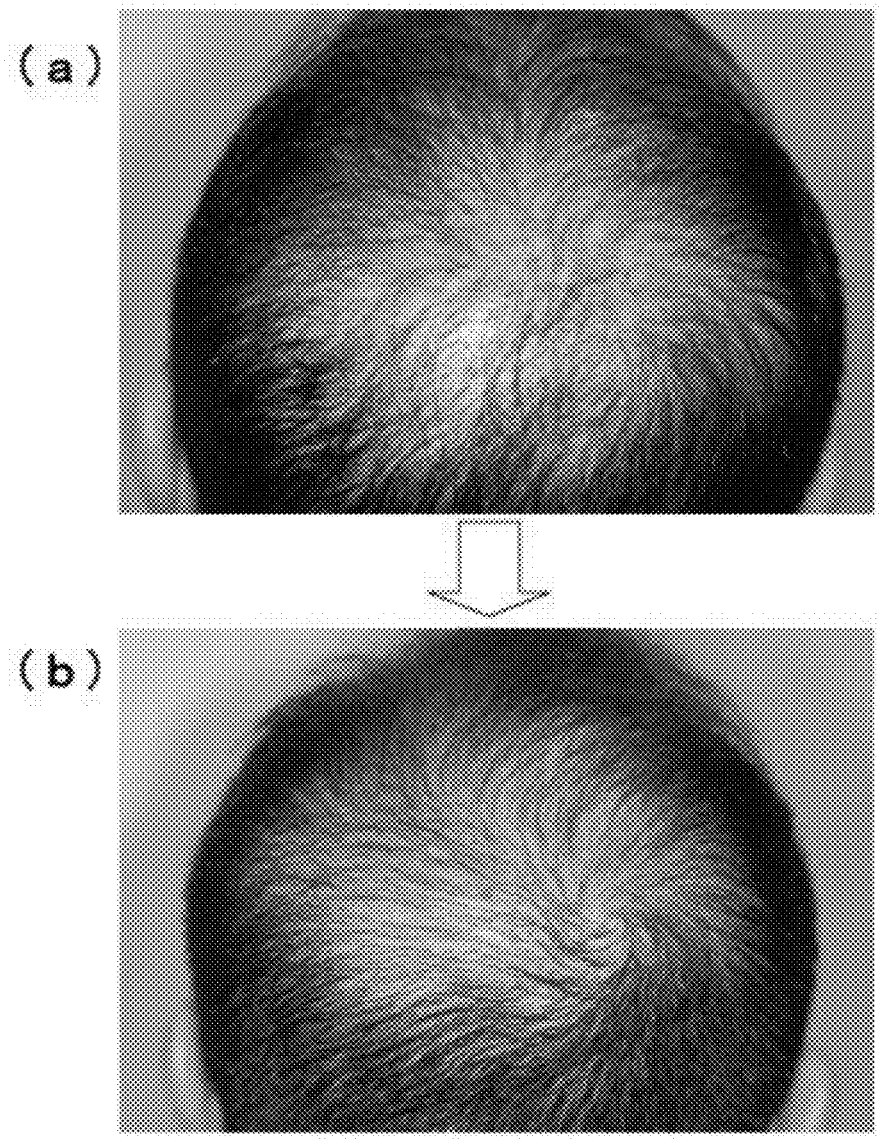
FIG. 16 is the status of the progress of hair restoration of male monitors 8.
Figure 17:
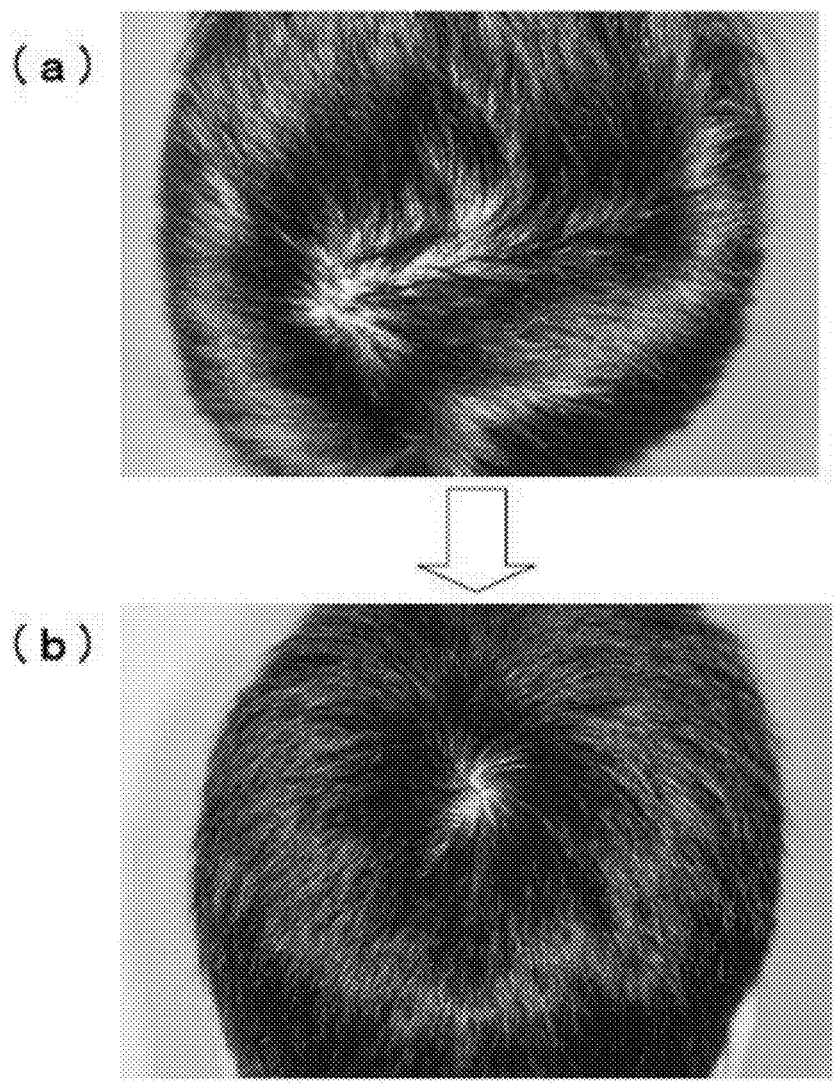
FIG. 17 is the status of the progress of hair restoration of male monitors 9.
Figure 18:
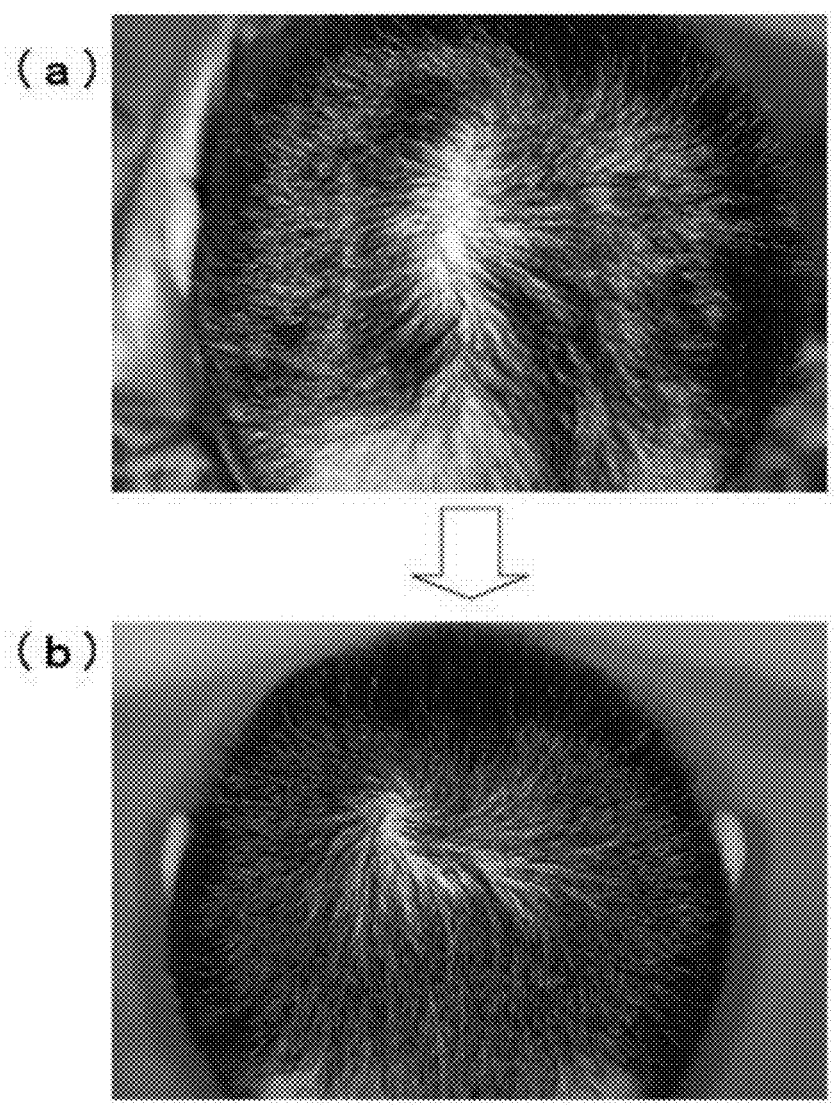
FIG. 18 is the status of the progress of hair restoration of male monitors 10.

Next, normal human fibroblasts were irradiated with the ultra-narrowband red, green, and blue lights having a half-band width of 10 nm or less for three days using the ultra-narrowband light irradiation means. The HGF concentration of the culture supernatant collected on the 4th day was measured by an ELISA kit. FIG. 8 shows the measurement results. As shown in FIG. 8, the measurement results indicated that the protein concentration significantly increased by the irradiation of all of the ultra-narrowband red, green, and blue lights having a half-band width of 10 nm or less.

Here, the roles of the cytokines, the changes of which were observed by RT-PCR, regarding hair growth are described. First, HGF acts on the induction and maintenance of the hair growth phase. IGF acts on organogenesis and the maintenance of the growth phase. Leptin acts on the induction of the hair growth phase. VEGF is a cytokine that is reported to be more increasingly secreted from hair papilla cells by the action of minoxidil, which is widely used in the treatment of androgenetic alopecia. VEGF has an effect of promoting angiogenesis of hair follicles. In contrast to these cytokines, which serve to promote hair growth, TNF-α is a cytokine that acts on the inhibition of hair growth, including the inhibition of the hair growth phase, the induction of the hair regression phase, etc.

The analysis of the above hair papilla cells by the RT-PCR assay indicates that the cytokines serving to promote hair growth tend to increase by the irradiation of the ultra-narrowband red and green lights having a half-band width of 10 nm or less, while the expression of TNF-α, which serves to inhibit hair growth, is inhibited by the irradiation of the ultra-narrowband red and green lights having a half-band width of 10 nm or less. These results suggest the possibility of promoting hair growth by the irradiation of the ultra-narrowband red and green lights having a half-band width of 10 nm or less.

Here, regarding the penetration depth of the ultra-narrowband red and green lights having a half-band width of 10 nm or less into the skin, a light of a longer wavelength generally has a deeper penetration depth, and therefore, the blue light of the shortest wavelength, which has a penetration depth of about 0.5 mm, is assumed to have less influence on human head hair papilla cells. The green light is also considered to have less influence on hair papilla cells in the growth phase, but may have sufficient influence on hair papilla cells in the resting phase. The penetration depth of the red light is considered to have sufficient influence on hair papilla cells.

Additionally, the use of the light-emitting diode (LED) as the irradiation source of the ultra-narrowband light having a half-band width of 10 nm or less results in the following advantages. That is, the irradiation output is very low, and tissue is less damaged, so that no downtime occurs after irradiation, and complications, such as pigmentation, are less likely to occur, compared to laser irradiation, etc. Since the use of the ultra-narrowband light having a half-band width of 10 nm or less allows irradiation of single-wavelength light, harmful wavelengths can be removed, and light of a plurality of wavelengths can be widely applied.

Furthermore, due to the use of the irradiation means using a light-emitting diode (LED), self-heating is less, and no cooling device is required. Thus, the device can be made compact and portable. Such a compact and portable device can improve convenience.

The following describes the results of actually irradiating human heads with an ultra-narrowband red light having a half-band width of 10 nm or less, while showing photograph data. As subjects, 10 male monitors aged between 29 and 58 (average age 48.1 years old) with confirmed hair-thinning on their scalps and were subjected to irradiation once a week on average for three months or more were prepared.

In the experimental method, as with the aforementioned hair papilla cells, the scalp of each patient as a monitor was irradiated with the ultra-narrowband red light in a distance of about 10 cm from the scalp for 20 minutes per time. Irradiation was carried out once to three times a week for each monitor (once a week or more on average) and the experiment period was between three and eight months. The monitors did not take any special treatment for their scalps such as use of a hair growing agent and unclogging of pores and carried out their normal daily routines. To determine the effects, the M-shaped thin hair part was excluded. Determination was conducted according to the criteria 1 to 3 in the following Table 4.

TABLE 4

| Determination | Expression | Condition |
|---|---|---|
| 1 Effective | Ia | 25% or more of region where skin could be seen due to thinning hair was reduced |
|  | Ib | Hair was visibly strong or hair was visibly straightened |
| 2 Very effective | IIa | 50% or more of region where skin could be seen due to thinning hair was reduced |
|  | IIb | Hair was visibly, significantly stronger or hair was significantly straightened |
| 3 Healed | IIIa | Condition of scalp returning approximately to a condition which is before hair started thinning |

The result of the progress of hair restoration of male monitors 1 to 10 is as shown in table 5 listed below. Moreover, FIGS. 9 to 18 show the status of the progress of hair restoration of male monitors 1 to 10.

TABLE 5

Figure 3:
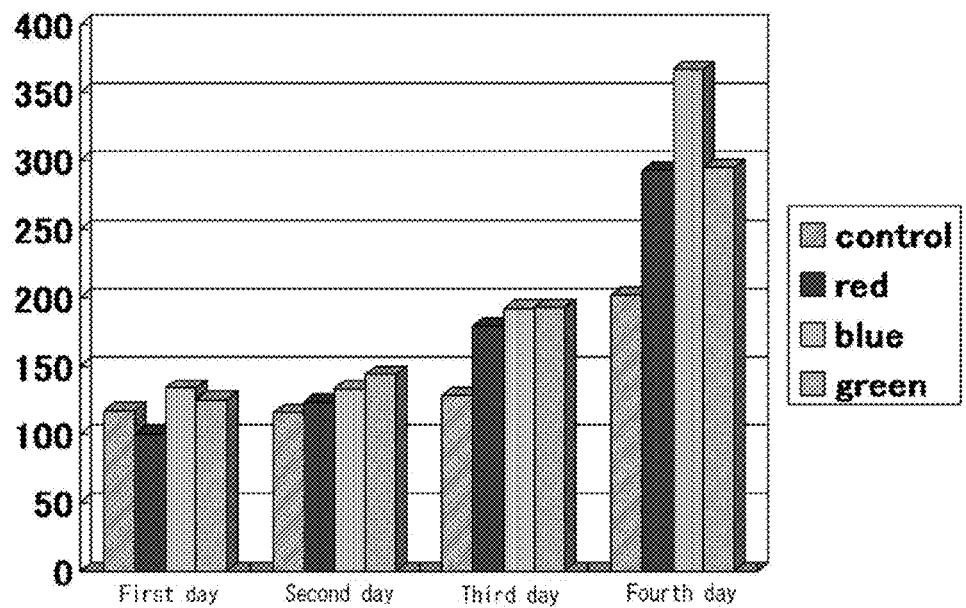
FIG. 3 is a drawing showing protein concentration analysis by the ELISA method (HGF).
Figure 4:
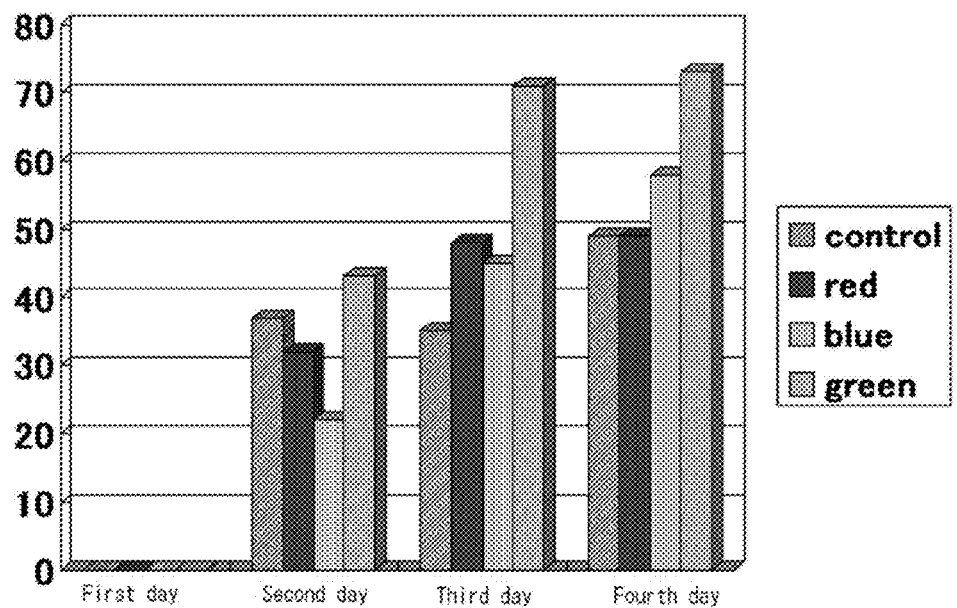
FIG. 4 is a drawing showing protein concentration analysis by the ELISA method (KGF).
Figure 5:
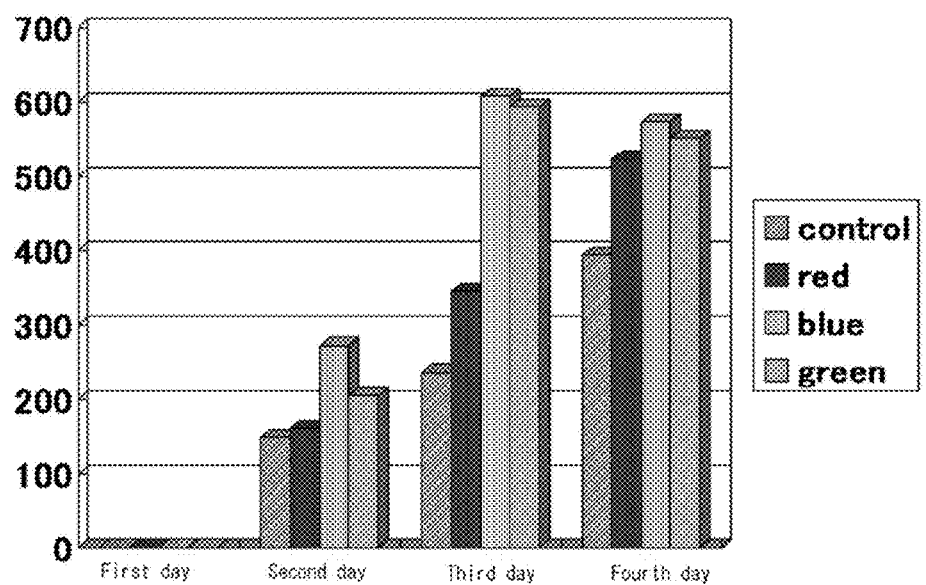
FIG. 5 is a drawing showing protein concentration analysis by the ELISA method (VEGF).
Figure 6:
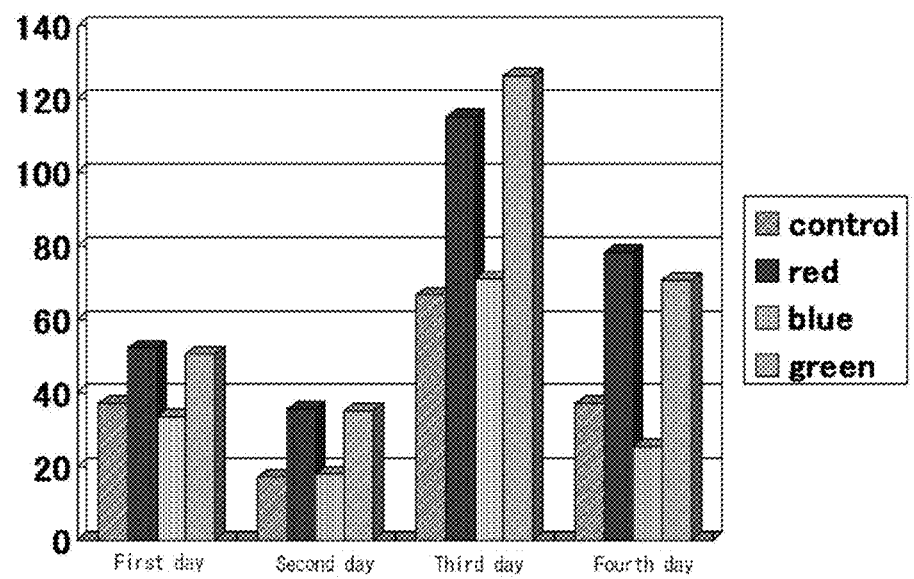
FIG. 6 is a drawing showing protein concentration analysis by the ELISA method (leptin).
Figure 7:
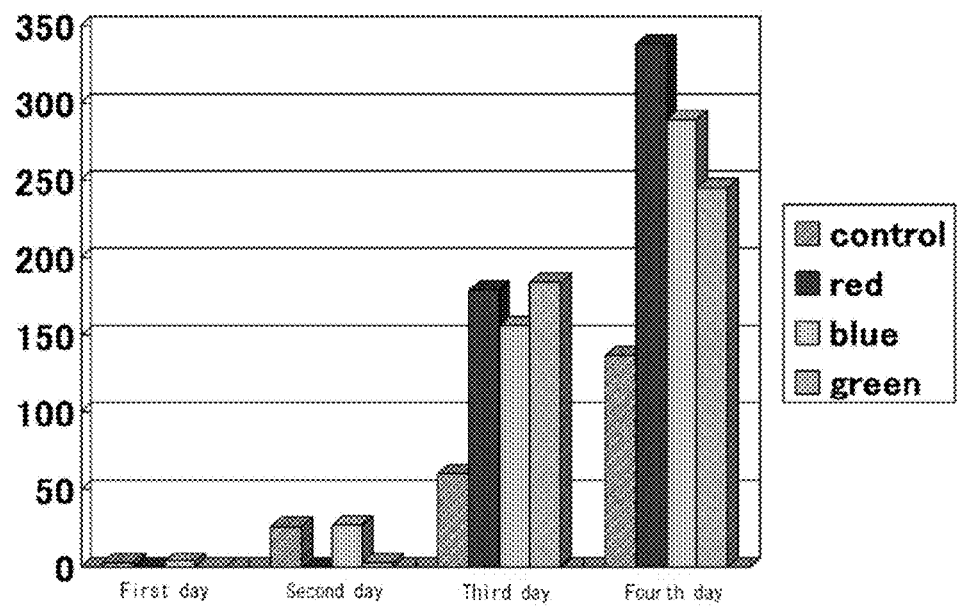
FIG. 7 is a drawing showing protein concentration analysis by the ELISA method (IL-8).

| No. | Clinical trials | Age | Hamilton classification | Hair treatment | Photographs of the treatment process | |
|---|---|---|---|---|---|---|
| A | monitor 1 | 55 | VI Type | Markedly (IIa) | FIG. 5-3 | (a) Pre-treatment |
|  |  |  |  |  |  | (b) After 17 weeks (32 times of Irradiation) |
| B | monitor 2 | 50 | VI Type | Markedly (IIa) | FIG. 5-6 | (a) Pre-treatment |
|  |  |  |  |  |  | (b) After 27 weeks (41 times of Irradiation) |
| C | monitor 3 | 54 | VI Type | Effective (Ib) | FIG. 5-9 | (a) Pre-treatment |
|  |  |  |  |  |  | (b) After 33 weeks (80 times of Irradiation) |
| D | monitor 4 | 29 | Va Type | Recovery (IIIa) | FIG. 5-2 | (a) After 8 weeks (15 times of Irradiation) |
|  |  |  |  |  |  | (b) After 18 weeks (33 times of Irradiation) |
|  |  |  |  |  |  | (c) After 26 weeks (50 times of Irradiation) |
| E | monitor 5 | 55 | V Type | Markedly (IIa) | FIG. 5-10 | (a) Pre-treatment |
|  |  |  |  |  |  | (b) After 54 weeks (128 times of Irradiation) |
| F | monitor 6 | 58 | V Type | Markedly (IIa) | FIG. 5-7 | (a) Pre-treatment |
|  |  |  |  |  |  | (b) After 11 weeks (14 times of Irradiation) |
| G | monitor 7 | 47 | IV Type | Markedly (IIa) | FIG. 5-11 | (a) Pre-treatment |

TABLE 5-continued

| No. | Clinical trials | Age | Hamilton classification | Hair treatment | | Photographs of the treatment process |
|---|---|---|---|---|---|---|
| H | monitor 8 | 45 | VI Type | Markedly (IIb) | FIG. 5-8 | (b) After 31 weeks (41 times of Irradiation)<br>(a) Pre-treatment<br>(b) After 19 weeks (19 times of Irradiation) |
| I | monitor 1 | 38 | IIIvertex Type | Recovery (IIIa) | FIG. 5-1 | (a) Pre-treatment<br>(b) After 21 weeks (29 times of Irradiation) |
| J | monitor 5 | 38 | IIIvertexn Type | Markedly (IIa) | FIG. 5-5 | (a) Pre-treatment<br>(b) After 9 weeks (20 times of Irradiation) |

In a case where irradiation was carried out once a week or more, the efficacy rate was 100%. Among them, thinning hair of two healed. Seven of the other monitors showed very effective results and one showed an effective result.

As a result of the above, all of the 10 monitors confirmed hair growth and the efficacy rate was 100%, while seven out of the 10 confirmed very effective results or more and two out of 10 confirmed restoration. In many cases, the effects appeared by the order of reduced hair loss, strength in hair and appearance of straightened hair, regeneration of hair whorl and visible hair growth (visible change from downy hair or vellus hair to strong hair). Moreover, little effect could be seen for M-shaped thin hair. In all of the above-mentioned 10 examples, effects could be confirmed visually within a few months.

Embodiment 3

Figure 19:
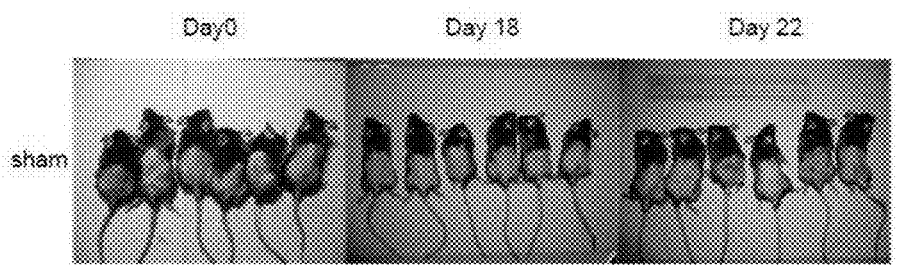
FIG. 19 is the results of hair restoration experiment of rats by narrow-band red LED irradiation (1).
Figure 20:
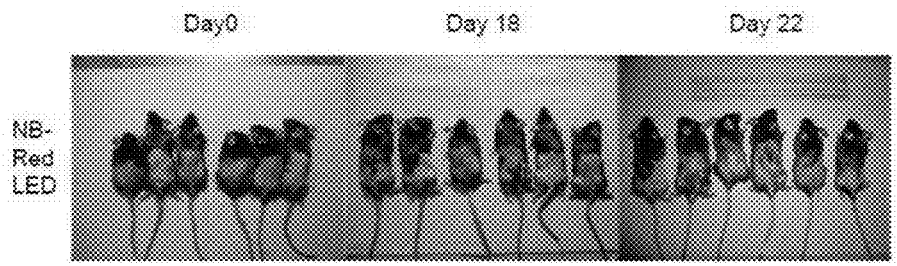
FIG. 20 is the results of hair restoration experiment of rats by narrow-band red LED irradiation (2).
Figure 21:
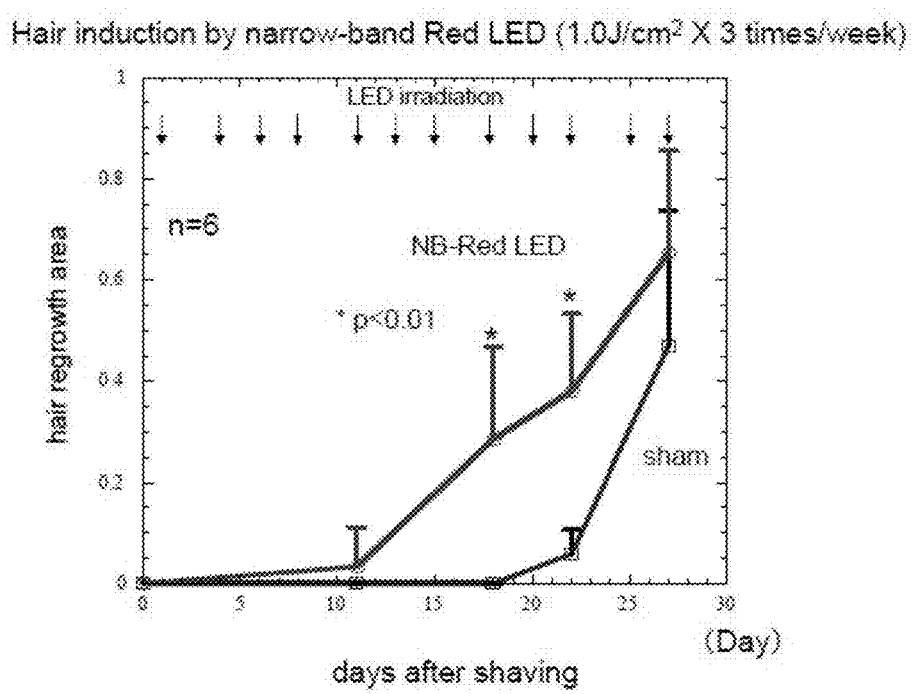
FIG. 21 is the graph of the results of hair restoration experiment of rats by narrow-band red LED irradiation.
Figure 22:
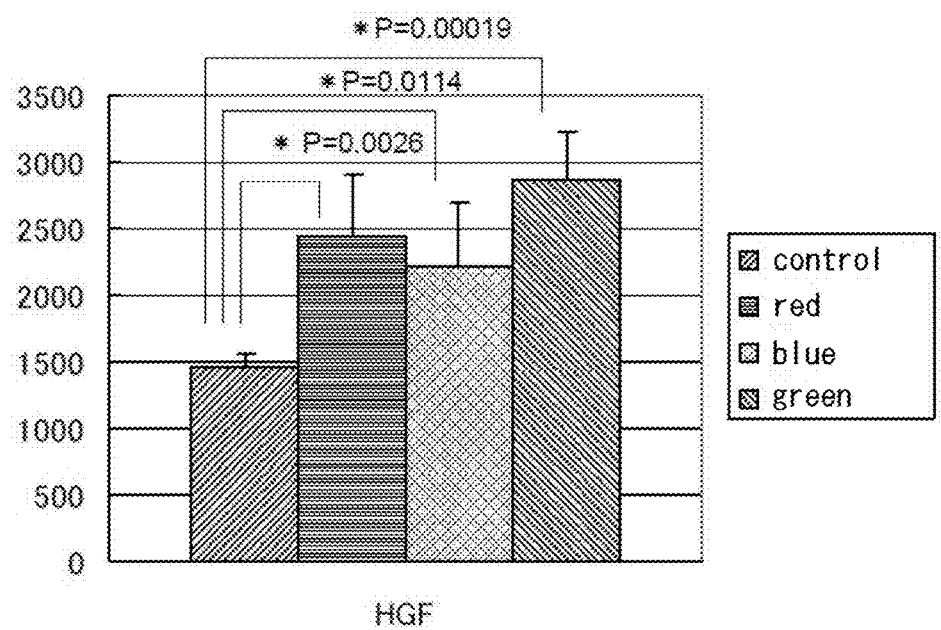
FIG. 22 is experimental results 1 of wound healing effects (HGF).
Figure 23:
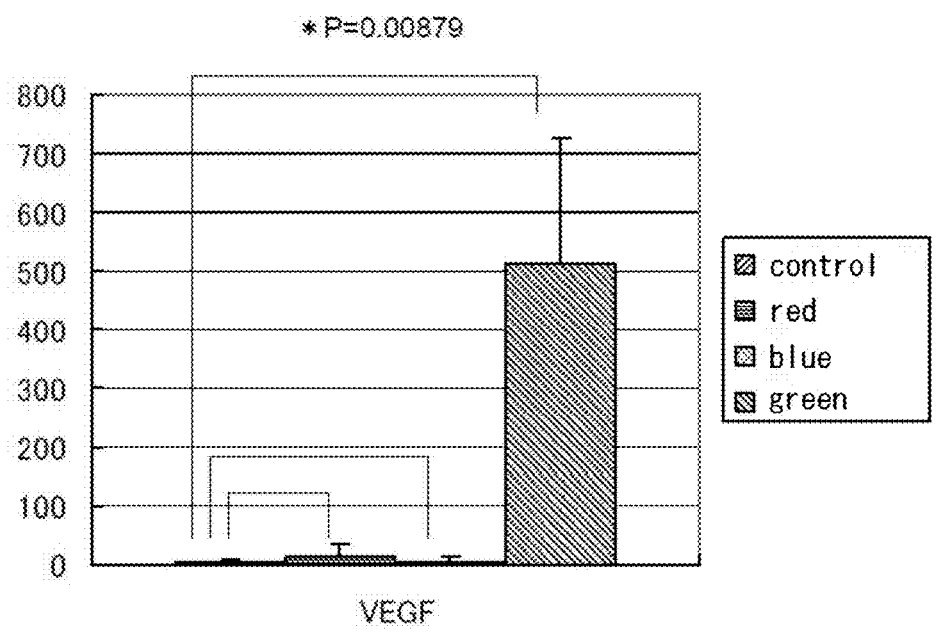
FIG. 23 is experimental results 2 of wound healing effects (VEGF).
Figure 24:
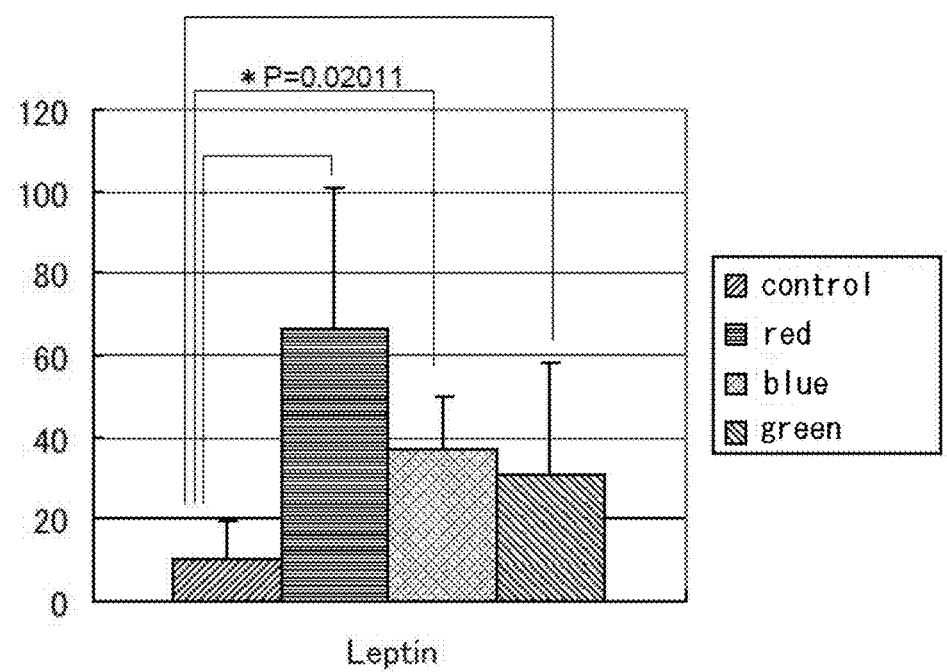
FIG. 24 is experimental results 3 of wound healing effects (leptin).
Figure 25:
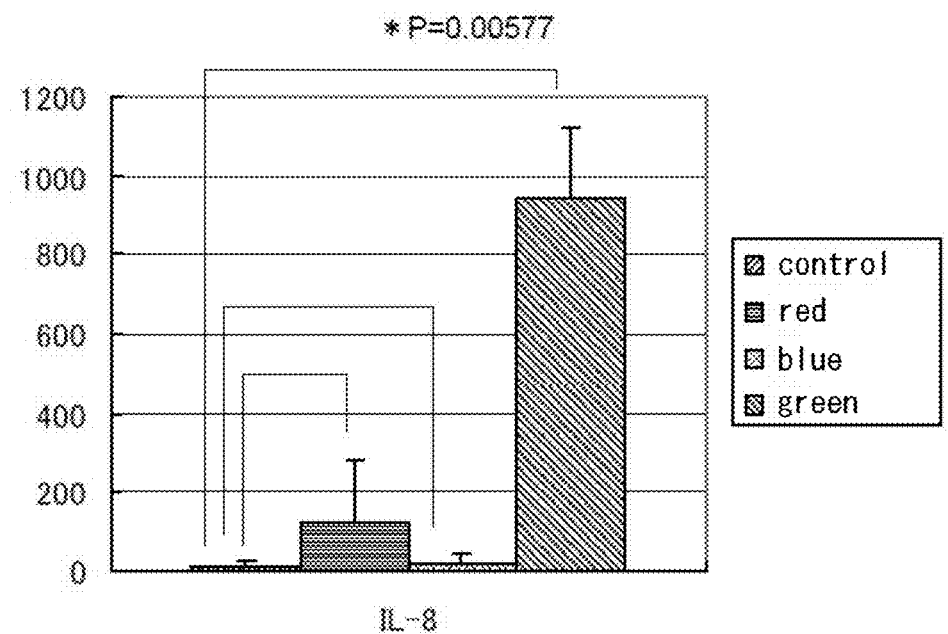
FIG. 25 is experimental results 4 of wound healing effects (IL-8).
Figure 26:
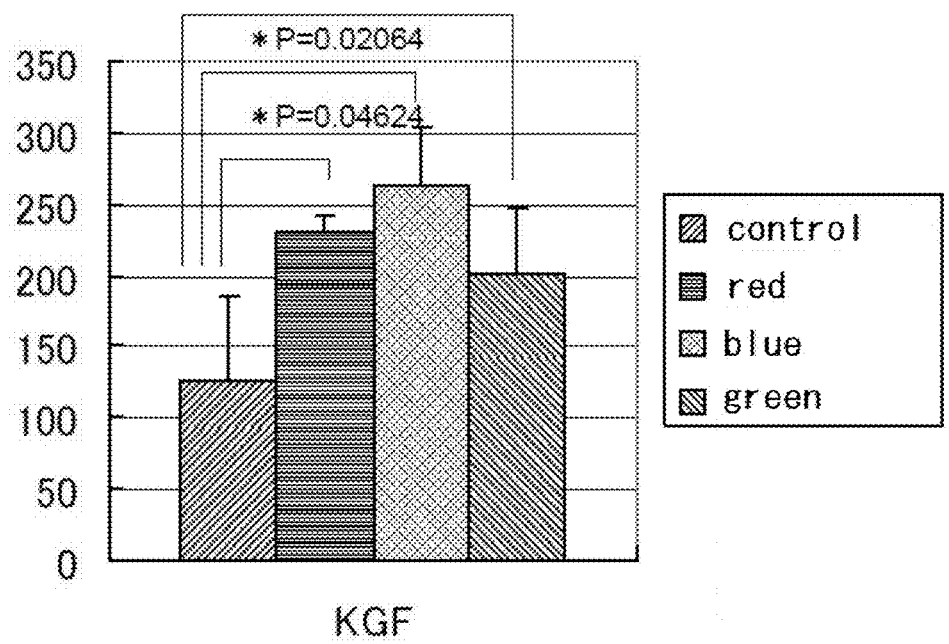
FIG. 26 is experimental results 5 of wound healing effects (KGF).

Example 3 describes the results of hair restoration experiment by the irradiation of a narrow-band red LED. FIGS. 19 to 21 show the results of hair restoration experiment of six rats by the irradiation of a narrow-band red LED. FIG. 19 shows the results of irradiating a commercially available red LED light, which was not narrow-band, as control subjects. On the other hand, FIG. 20 shows the results of irradiating a narrow-band red LED (NB-Red LED) light having a half-band width of 10 nm. The wavelength of the red LED used in the experiment is 635 nm.

FIG. 21 shows a graph indicating the extent of the hair restoration area as a result of the irradiation experiment using the narrow-band red LED light and the commercially available red LED light. In FIG. 21, the horizontal axis indicates the number of elapsed days after shaving, and the vertical axis numerically indicates hair growth area in the range of 0 (no hair grew) to 1 (hair grew in the entire body). In addition, the arrows shown in the upper part of the graph of FIG. 21 indicate the number of times and timing of light irradiation. The light irradiation was performed three times a week for four weeks.

The light irradiation energy was 1.0 (J/cm$^2$).

According to the graph of FIG. 21, the hair of mice irradiated with the narrow-band red LED light started to grow in 11 days after the start of the irradiation, whereas the hair of mice irradiated with the commercially available non-narrow-band red LED light started to grow in 22 days after the start of the irradiation. Moreover, in four weeks after the start of the irradiation, mice irradiated with the narrow-band red LED light showed 60% or more of hair growth area, whereas mice irradiated with the commercially available non-narrow-band red LED light showed only about 50% of hair growth area. These results demonstrate that the narrow-band red LED light has a more excellent hair restoration effect than the non-narrow-band red LED light.

Embodiment 4

In Example 4, wound healing effects were observed by using a narrow-band LED having a half-band width of 10 nm. Normal human fibroblasts were used in the observation. First, 6-mm skin defects were generated in diabetic model mice, and irradiated with a narrow-band LED red, blue, or green light having a half-band width of 10 nm. FIGS. 22 to 26 show the results of HGF, VEGF, leptin, IL-8, and KGF, respectively.

In the case of using the green narrow-band LED, remarkable effects were observed in VEGF and IL-8. In addition, the green narrow-band LED had the most effect on HGF, compared to the other color LEDs.

In the case of using the red narrow-band LED, the most effect was observed in leptin, compared to the other color LEDs. In the case of using the red narrow-band LED, more significant effects were observed in HGF, IL-8, and KGF, compared to the control mice. These results demonstrate that in the case of the irradiation of narrow-band LED light having a half-band width of 10 nm, wound healing effects can be obtained by using green and red narrow-band LEDs.

The wound healing effects can be increased by alternately irradiating these two green and red lights. When the two green and red lights are irradiated simultaneously, the lights interfere with each other, reducing the wound healing effects. The interferential action of the two lights can be avoided by alternately irradiating the green and red lights. In addition, since the red light permeates more deeply under the skin than the green light, the device using the red light is expected to enhance the wound healing effects.

INDUSTRIAL APPLICABILITY

The present invention is useful for skin wound treatment devices and hair restoration devices in hospital.

DESCRIPTION OF SYMBOLS

1. Ultra-narrowband light irradiation means
2. Ultra-narrowband light irradiation means
111. Fibroblasts
112. Keratin-producing cells
113. Macrophages
114. Endothelial cells

What is claimed is:

1. A method for promoting hair restoration comprising:
obtaining a device which generates a red light beam having a peak wavelength of 630 to 650 nm and a half-band width (full width half maximum) of 10 nm or less;
applying the red light beam to a scalp with a diffusing lens for at least 20 minutes with an irradiation energy of at least 0.6 J/cm$^2$ at a distance of 10 cm from an irradiation light source; and thereby changing a respective mRNA expression level of each of the following cytokines within 24 hours after the red light beam was applied: HGF (Hepatocyte Growth Factor), IGF (Insulin-like growth factors), and VEGF (Vascular Endothelial Growth Factor) from hair papilla cells.

2. The method of claim 1, further comprising changing an mRNA expression level the cytokine leptin within 24 hours after the red light beam was applied.

3. The method of claim 2, further comprising decreasing an mRNA expression level of cytokine TNF-α within eight hours after the red light beam was applied.

4. The method of claim 1, further comprising decreasing an mRNA expression level of cytokine TNF-α within eight hours after the red light beam was applied.

5. A method comprising:
obtaining a device which generates a red light having a peak wavelength of 630 to 650 nm and a half-band width of 10 nm or less;
performing at least one light irradiation by applying the red light to a person's head for at least 20 minutes with an irradiation energy of at least 0.6 J/cm$^2$ at a distance of 10 cm from an irradiation light source; and
thereby increasing mRNA expression levels of cytokines secreted from hair papilla cells, as a result of the red light irradiation, wherein the cytokines are HGF (Hepatocyte Growth Factor), IGF (Insulin-like growth factors), and VEGF (Vascular Endothelial Growth Factor), which are cell growth factors, the mRNA expression levels of each of these cytokines being increased within 24 hours after the light irradiation.

6. The method of claim 5, wherein increasing mRNA expression levels of cytokines secreted from hair papilla cells, as a result of the red light irradiation, comprises increasing mRNA expression levels of leptin within 24 hours after the light irradiation.

* * * * *